(12) United States Patent
Brown et al.

(10) Patent No.: US 6,872,719 B1
(45) Date of Patent: Mar. 29, 2005

(54) PHENYLALANINE ENAMIDE DERIVATIVES

(75) Inventors: Julien Alistair Brown, Reading (GB); Stuart Bailey, Dorking (GB); Stephen Brand, Reading (GB)

(73) Assignee: Celltech R & D Limited (GB)

( * ) Notice: Subject to any disclaimer, the term of this patent is extended or adjusted under 35 U.S.C. 154(b) by 64 days.

(21) Appl. No.: 10/620,533

(22) Filed: Jul. 16, 2003

(30) Foreign Application Priority Data

Jul. 17, 2002 (GB) .............................................. 0216568

(51) Int. Cl.$^7$ .................. A61K 31/5377; A61K 31/496; A61K 31/44; C07D 401/12; C07D 413/12
(52) U.S. Cl. .............................. 514/237.8; 514/252.12; 514/278; 544/70; 544/230; 546/15
(58) Field of Search ..................... 544/70, 230; 546/15; 514/237.8, 252.12, 278

(56) References Cited

FOREIGN PATENT DOCUMENTS

WO      WO 02/068393 A1      9/2002

OTHER PUBLICATIONS

Abraham, W.M. et al., "$\alpha_4$–Integrins Mediate Antigen–Induced Late Bronchial Responses and Prolonged Airway Hyperresponsiveness in Sheep," *J. Clin. Invest.*, 1994, 93, 776–787.
Berlin, C. et al., "α4β7 Integrin Mediates Lymphocyte Binding to the Mucosal Vascular Addressin MAdCAM–1," *Cell*, 1993, 74, 185–195.
Binns, R.M. et al., "The Role of E–Selectin in Lymphocyte and Polymorphonuclear Cell Recruitment into Cutaneous Delayed Hypersensitivity Reactions in Sensitized Pigs," *J. Immunol.*, 1996, 157, 4094–409.
Tiskin, M.J., et al., "Structural requirements for mucosal vascular addressin binding to its lymphocyte receptor $\alpha_4\beta_7$," *J. Immunol.*, 1996, 156, 719–726.
Brooks, Peter C., et al., "Antiintegrin αvβ3 blocks human breast cancer growth and angiogenesis in human skin," *J. Clin. Invest.*, 1995, 96, 1815–1822.
Cardarelli, P.M. et al., "Cyclic RGD Peptide Inhibits α4β7 Interaction with Connecting Segment 1 and Vascular Cell Adhesion Molecule," *J. Biol. Chem.*, 1994, 269(28), 18668–18673.
Erle, D.J., et al., "Expression and function of the Mad-CAM–1 receptor, integrin α4β7, on human leukocytes," *J. Immunol.*, 1994, 153, 517–528.
Ferguson, T.A. et al., "Two integrin–binding peptides abrogate T cell–mediated immune responses in vivo," *Proc. Natl. Acad. Sci. USA*, 1991, 88, 8072–8076.
Hammes, H., et al., "Subcutaneous injection of a cyclic peptide antagonist of vitronectin receptor–type integrins inhibits retinal neovascularization," *Nature Medicine*, 1996, 2, 529–533.

Hesterberg, P.E., et al., "Rapid resolution of chronic colitis in the cotton–top tamarin with an antibody to a gut–homing integrin α4β7," *Gastroenterol*, 1996, 111, 1373–1380.
Hodivala–Dilke, K.M., "β3–integrin–deficient mice are a model for glanzmann thrombasthenia showing placental defects and reduced survival," *J. Clin. Invest.*, 1999, 103(2), 229–238.

(Continued)

*Primary Examiner*—Laura L. Stockton
(74) *Attorney, Agent, or Firm*—Woodcock Washburn LLP

(57) ABSTRACT

Phenylalanine enamide derivatives of formula (1) are described:

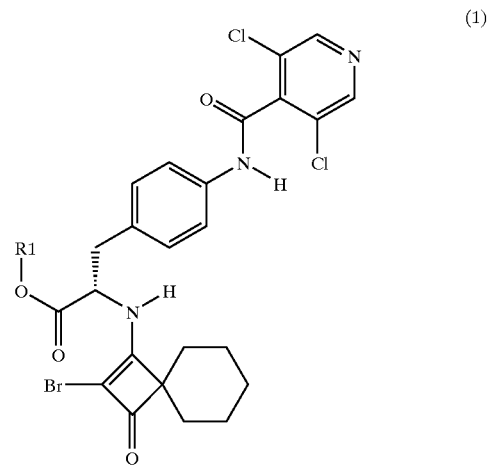

(1)

wherein R$^1$ is a —CH$_3$, —(CH$_2$)$_3$CH$_3$, —CH$_2$CH$_2$OH, —CH$_2$CH$_2$OCH$_3$, —CH$_2$CH$_2$OCH$_2$CH$_2$OH, —CH$_2$CH$_2$OCH$_2$CH$_2$OCH$_3$,

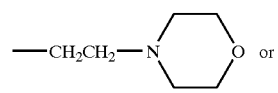 or

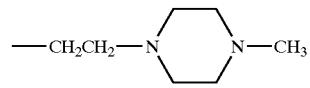

group;
and the salts, solvates and N-oxides thereof.

Compounds according to the invention are potent and selective inhibitors of α4 integrins. The compounds are of use in modulating cell adhesion and in particular are of use in the prophylaxis and treatment of diseases or disorders including inflammation in which the extravasation of leukocytes plays a role and the invention extends to such a use and to the use of the compounds for the manufacture of a medicament for treating such diseases or disorders.

8 Claims, No Drawings

OTHER PUBLICATIONS

Holzmann, B., et al., "Peyer's patch–specific lymphocyte homing receptors consist of a VLA–4–like α chain associated with either of two integrin β chains, one of which is novel," *EMBO J.*, 1989, 8(6), 1735–1741.

Humphries, M.J. et al., "Mechanisms of VCAM–1 and fibronectin binding to integrin $\alpha_4\beta_1$: implications for integrin function and rational drug design," *Ciba Foundation Symposium*, 1995, 189, 177–194.

Issekutz, T.B., "Inhibition of Lymphocyte Endothelial Adhesion and In Vivo Lymphocyte Migration to Cutaneous Inflammation by TA–3, a New Monoclonal Antibody to Rat LFA–1," *J. Immunol.*, 1992, 149(10), 3394–3402.

Li, Z. et al., "Effect of an anti–Mo1 MAb on ozone–induced airway inflammation and airway hyperresponsiveness in dogs," *Am. J. Physiol.*, 1992, 263(6 Pt 1), L723–726.

Marlin, S.D. et al., "LFA–1 Immunodeficiency Disease," *J. Exp. Med.*, 1986, 164, 855–867.

Mitjans, F., et al., "An anti–αv–integrin antibody that blocks integrin function inhibits the development of a human melanoma in nude mice," *J. Cell Science*, 1995, 108, 2825–2838.

Newham, P., et al., "Integrin adhesion receptors: structure, function and implications for biomedicine," *Molecular Medicine Today*, 1996, 304–313.

Osborne, L., "Leukoctye Adhesion to Endothelium in Inflammation," *Cell*, 1990, 62, 3–6.

Podolsky, D.K. et al., "Attenuation of Colitis in the Cotton–top Tamarin by Anti–α4 integrin Monoclonal Antibody," *J. Clin. Invest.*, 1993, 92, 372–380.

Shroff, H.N., et al., "Small peptide inhibitors of $\alpha_4\beta_7$ mediated MadCAM–1 adhesion to lymphocytes," *Biorg. Med. Chem. Letts.*, 1996, 6(21), 2495–2500.

Sonnenberg, A., "Integrins and their ligands," *Curr. Topics Microbiol. Immunol.*, 1993, 184, 7–35.

Springer, T.A., "Adhesion receptors of the immune system," *Nature*, 1990, 346, 425–434.

Springer, T.A., "Traffic Signals for Lymphocyte Recirculation and Leukocyte Emigration: The Multistep Paradigm," *Cell*, 1994, 76, 301–314.

Srivatsa, S.S., et al., "Selective $\alpha v\beta 3$ integrin blockade potently limits neointimal hyperplasia and lumen stenosis following deep coronary arterial stent injury: evidence for the functional importance of integrin $\alpha v\beta 3$ and osteopontin expression during neointima formation," *Cariovascular Research*, 1997, 36, 408–428.

Vanderslice, P. et al., "A Cyclic Hexapeptide is a Potent Antagonist of α4 Integrins," *J. Immunol.*, 1997, 158, 1710–1718.

Wasserman, H.H., et al., "Cyclobutenone derivatives from ethoxyacety;ene," *J. Org. Chem.*, 1973, 38(8), 1451–1455.

Yang, X., "A predominant role of integrin α4 in the spontaneous development of autoimmune diabetes in nonobese diabetic mice," *Proc. Natl. Acad. Sci. USA*, 1994, 91, 12604–12608.

Yednock, T.A., "Prevention of experimental autoimmune encephalomyelitis by antibodies against α4β1 integrin," *Nature*, 1992, 356, 63–66.

PHENYLALANINE ENAMIDE DERIVATIVES

This application claims the benefit under 35 U.S.C. § 119 (a)–(d) of United Kingdom Application No. GB 0216568.6, filed Jul. 17, 2002, which is incorporated herein by reference in its entirety.

This invention relates to a number of phenylalanine enamide esters, to compositions containing them, to processes for their preparation, and to their use in medicine.

Over the last few years it has become increasingly clear that the physical interaction of inflammatory leukocytes with each other and other cells of the body plays an important role in regulating immune and inflammatory responses [Springer, T. A., Nature, 346, 425, (1990); Springer, T. A., Cell, 76, 301, (1994)]. Specific cell surface molecules collectively referred to as cell adhesion molecules mediate many of these interactions.

The adhesion molecules have been sub-divided into different groups on the basis of their structure. One family of adhesion molecules which is believed to play a particularly important role in regulating immune and inflammatory responses is the integrin family. This family of cell surface glycoproteins has a typical non-covalently linked heterodimer structure. At least 16 different integrin alpha chains and 8 different integrin beta chains have been identified [Newman, P. et al, Molecular Medicine Today, 304, (1996)]. The members of the family are typically named according to their heterodimer composition although trivial nomenclature is widespread in the field. Thus the integrin $\alpha 4\beta 1$ consists of the integrin alpha 4 chain associated with the integrin beta 1 chain, but is also widely referred to as Very Late Antigen 4 or VLA-4. Not all of the potential pairings of integrin alpha and beta chains have yet been observed in nature and the integrin family has been subdivided into a number of subgroups based on the pairings that have been recognised to date [Sonnenberg, A., Current Topics in Microbiology and Immunology, 184, 7, (1993)].

The importance of integrin function in normal physiological responses is highlighted by two human deficiency diseases in which integrin function is defective. Thus in the disease termed Leukocyte Adhesion Deficiency (LAD) there is a defect in one of the families of integrins expressed on leukocytes [Marlin, S. D. et al, J. Exp. Med. 164, 855, (1986)]. Patients suffering from this disease have a reduced ability to recruit leukocytes to inflammatory sites and suffer recurrent infections, which in extreme cases may be fatal. In the case of patients suffering from the disease termed Glanzman's thrombasthenia (a defect in a member of the beta 3 integrin family) there is a defect in blood clotting [Hodivala-Dilke, K. M., J. Clin. Invest. 103, 229, (1999)].

The potential to modify integrin function in such a way as to beneficially modulate cell adhesion has been extensively investigated in animal models using specific antibodies and peptides that block various functions of these molecules [e.g. Issekutz, T. B., J. Immunol. 149, 3394, (1992); Li, Z. et al, Am. J. Physiol. 263, L723, (1992); Mitjans, F. et al, J. Cell Sci. 108, 2825, (1995); Brooks, P. C. et al, J. Clin. Invest. 96, 1815, (1995); Binns, R. M. et al, J. Immunol. 157, 4094, (1996); Hammes, H.-P. et al, Nature Medicine 2, 529, (1996); Srivata, S. et al, Cardiovascular Res. 36, 408 (1997)]. In particular an anti $\alpha_4\beta_7$-antibody has demonstrated both clinical and histologic improvement of inflammatory activity and disease in a non-human primate model of inflammatory bowel disease [Hesterberg, P. E. et a, Gastroenterol, 111, 1373–80 (1996)]. A number of monoclonal antibodies which block integrin function are currently being investigated for their therapeutic potential in human disease, and one, ReoPro, a chimeric antibody against the platelet integrin $\alpha IIb\beta 3$ is in use as a potent anti-thrombotic agent for use in patients with cardiovascular complications following coronary angioplasty.

Integrins recognize both cell surface and extracellular matrix ligands, and ligand specificity is determined by the particular alpha-beta subunit combination of the molecule [Newman, P., ibid]. One particular integrin subgroup of interest involves the $\alpha 4$ chain which can pair with two different beta chains $\beta 1$ and $\beta 7$ [Sonnenberg, A., ibid]. The $\alpha 4\beta 1$ pairing occurs on many circulating leukocytes (for example lymphocytes, monocytes, eosinophils and basophils) although it is absent or only present at low levels on circulating neutrophils. $\alpha 4\beta 1$ binds to an adhesion molecule (Vascular Cell Adhesion Molecule-1 also known as VCAM-1) frequently up-regulated on endothelial cells at sites of inflammation [Osborne, L., Cell, 62, 3, (1990)]. The molecule has also been shown to bind to at least three sites in the matrix molecule fibronectin [Humphries, M. J. et al, Ciba Foundation Symposium, 189, 177, (1995)]. Based on data obtained with monoclonal antibodies in animal models it is believed that the interaction between $\alpha 4\beta 1$ and ligands on other cells and the extracellular matrix plays an important role in leukocyte migration and activation [Yednock, T. A. et at, Nature, 356, 63, (1992); Podolsky, D. K. et al, J. Clin. Invest. 92, 372, (1993); Abraham, W. M. et al, J. Clin. Invest. 93, 776, (1994)].

The integrin generated by the pairing of $\alpha 4$ and $\beta 7$ has been termed LPAM-1 [Holzmann, B. and Weissman, I. L., EMBO J. 8, 1735, (1989)]. The $\alpha 4\beta 7$ pairing is expressed on certain sub-populations of T and B lymphocytes and on eosinophils [Erle, D. J. et al, J. Immunol. 153, 517 (1994)]. Like $\alpha 4\beta 1$, $\alpha 4\beta 7$ binds to VCAM-1 and fibronectin. In addition, $\alpha 4\beta 7$ binds to an adhesion molecule believed to be involved in the homing of leukocytes to mucosal tissue such as gastrointestinal mucosa termed MAdCAM-1 [Berlin, C. et at, Cell, 74, 185, (1993)]. MAdCAM-1 is preferentially expressed in the gastrointestinal track. The interaction between $\alpha 4\beta 7$ and MAdCAM-1 may also be important at sites of inflammation outside of mucosal tissue [Yang, X.-D. et al, PNAS, 91, 12604, (1994)].

Regions of the peptide sequence recognized by $\alpha 4\beta 1$ and $\alpha 4\beta 7$ when they bind to their ligands have been identified. $\alpha 4\beta 1$ seems to recognise LDV, IDA or REDV peptide sequences in fibronectin and a QIDSP sequence in VCAM-1 [Humphries, M. J. et al, ibid] whilst $\alpha 4\beta 7$ recognises a LDT sequence in MAdCAM-1 [Birskin, M. J. et al, J. Immunol. 156, 719, (1996)]. There have been several reports of inhibitors of these interactions being designed from modifications of these short peptide sequences [Cardarelli, P. M. et al, J. Biol. Chem., 269, 18668, (1994); Shorff, H. N. et al, Biorganic Med. Chem. Lett., 6, 2495, (1996); Vanderslice, P. et al, J. Immunol., 158, 1710, (1997)]. It has also been reported that a short peptide sequence derived from the $\alpha 4\beta 1$ binding site in fibronectin can inhibit a contact hypersensitivity reaction in a trinitrochlorobenzene sensitised mouse [Ferguson, T. A., et al, PNAS, 88, 8072, (1991)].

Since the alpha 4 subgroup of integrins are predominantly expressed on leukocytes their inhibition can be expected to be beneficial in a number of immune or inflammatory disease states. However, because of the ubiquitous distribution and wide range of functions performed by other members of the integrin family it is important to be able to identify selective inhibitors of the alpha 4 subgroup.

We have now found a number of esters which are potent and selective inhibitors of $\alpha 4$ integrins. The compounds are able to inhibit $\alpha 4$ integrins such as $\alpha 4\beta 1$ and/or $\alpha 4\beta 7$, in for example cellular assays such as those described herein, at concentrations at which they generally have no or minimal inhibitory action on a integrins of other subgroups.

Thus according to one aspect of the invention we provide a compound of formula (1):

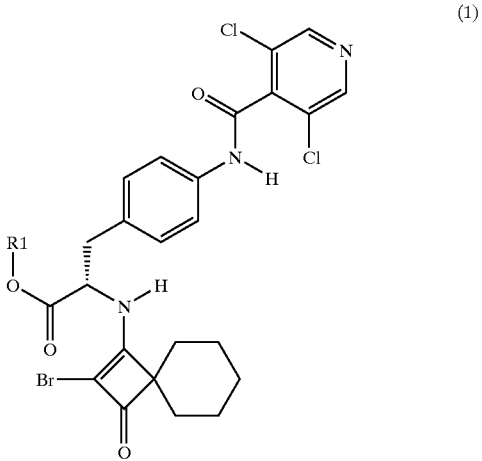

(1)

wherein $R^1$ is a —CH$_3$, —(CH$_2$)$_3$CH$_3$, —CH$_2$CH$_2$OH, —CH$_2$CH$_2$OCH$_3$, —CH$_2$CH$_2$OCH$_2$CH$_2$OH, —CH$_2$CH$_2$OCH$_2$CH$_2$OCH$_3$,

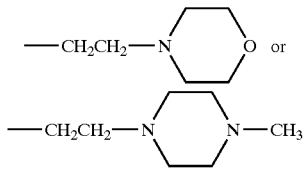

group;
and the salts, solvates and N-oxides thereof.

It will be appreciated that compounds of formula (1) may exist as enantiomers or diastereomers. The invention is to be understood to extend to all such enantiomers, diastereomers and mixtures thereof, including racemates. Formula (1) is intended to represent all individual isomers and mixtures thereof, unless stated or shown otherwise.

Salts of compounds of the invention include pharmaceutically acceptable salts, for example acid addition salts derived from inorganic or organic acids.

Acid addition salts include hydrochlorides, hydrobromides, hydroiodides, alkylsulphonates, e.g. methanesulphonates, ethanesulphonates, or isothionates, arylsulphonates, e.g. p-toluenesulphonates, besylates or napsylates, phosphates, sulphates, hydrogen sulphates, acetates, trifluoroacetates, propionates, citrates, maleates, fumarates, malonates, succinates, lactates, oxalates, tartrates and benzoates.

Particularly useful salts of compounds according to the invention include pharmaceutically acceptable salts, especially acid addition pharmaceutically acceptable salts.

The compounds of the invention are:
2-methoxyethyl (2S)-2-(2-bromo-3-oxo-spiro[3,5]non-1-en-1-ylamino)-3-{4-[(3,5-dichloroisonicotinoyl)amino]phenyl}propanoate and the salts, solvates and N-oxide thereof;
2-(2-hydroxyethoxy)ethyl (2S)-2-(2-bromo-3-oxo-spiro[3,5]non-1-en-1-ylamino)-3-{4-[(3,5-dichloroisonicotinoyl)amino]phenyl}propanoate and the salts, solvates and N-oxide thereof;
2-(2-methoxyethoxy)ethyl (2S)-2-(2-bromo-3-oxo-spiro[3,5]non-1-en-1-ylamino)3-{4-[(3,5-dichloroisonicotinoyl)amino]phenyl}propanoate and the salts, solvates and N-oxide thereof;
2-(morpholin-4-yl)ethyl (2S)-2-(2-bromo-3-oxo-spiro[3,5]non-1-en-1-ylamino)-3-{4-[(3,5-dichloroisonicotinoyl)amino]phenyl}propanoate and the salts, solvates and N-oxide thereof;
2-(4-methylpiperazin-1-yl)ethyl (2S)-2-(2-bromo-3-oxo-spiro[3,5]non-1-en-1-ylamino)-3-{4-[(3,5-dichloroisonicotinoyl)amino]phenyl}propanoate and the salts, solvates and N-oxide thereof;
and more particularly:
butyl (2S)-2-(2-bromo-3-oxo-spiro[3,5]non-1-en-1-ylamino)-3-{4-[(3,5-dichloroisonicotinoyl)amino]phenyl}propanoate and the salts, solvates and N-oxide thereof;
2-hydroxyethyl (2S)-2-(2-bromo-3-oxo-spiro[3.5]non-1-en-1-ylamino)-3-{4-[(3,5-dichloroisonicotinoyl)amino]phenyl}propanoate and the salts, solvates and N-oxide thereof;
methyl (2S)-2-(2-bromo-3-oxo-spiro[3,5]non-1-en-1-ylamino)-3-{4-[(3,5-dichloroisonicotinoyl)amino]phenyl}propanoate and the salts, solvates and N-oxide thereof.

The compounds according to the invention are potent and selective inhibitors of α4 integrins. The ability of the compounds to act in this way may be simply determined by employing tests such as the cellular assays described in the Examples hereinafter.

The compounds are of use in modulating cell adhesion and in particular are of use in the prophylaxis and treatment of diseases or disorders including inflammation in which the extravasation of leukocytes plays a role and the invention extends to such a use and to the use of the compounds for the manufacture of a medicament for treating such diseases or disorders.

Diseases or disorders of this type include inflammatory arthritis such as rheumatoid arthritis, vasculitis or polydermatomyositis, multiple sclerosis, allograft rejection, diabetes, inflammatory dermatoses such as psoriasis or dermatitis, asthma and inflammatory bowel disease.

For the prophylaxis or treatment of disease the compounds according to the invention may be administered as pharmaceutical compositions, and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrroliddne or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, nonaqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds for formula (1) may be formulated for parenteral administration by injection e.g. by bolus injection or infusion. Formulations for injection may be presented in unit dosage form, e.g. in glass ampoule or multi dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (1) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichloro-fluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

The quantity of a compound of the invention required for the prophylaxis or treatment of a particular condition will vary depending on the compound chosen, and the condition of the patient to be treated. In general, however, daily dosages may range from around 100 ng/kg to 100 mg/kg e.g. around 0.01 mg/kg to 40 mg/kg body weight for oral or buccal administration, from around 10 ng/kg to 50 mg/kg body weight for parenteral administration and around 0.05 mg to around 1000 mg e.g. around 0.5 mg to around 1000 mg for nasal administration or administration by inhalation or insufflation.

The esters of formula (1) may be prepared according to the processes described in the Examples hereinafter. In general this involves esterification of an intermediate acid of formula (2):

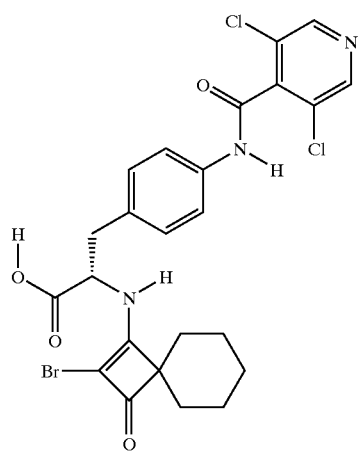

(2)

using standard methods known to those skilled in the art, such as reaction with an alcohol of formula R1OH in the presence of an acid catalyst e.g. p-toluenesulfonic acid. Alternatively a condensing agent, for example a diimide such as 1-(3-dimethylaminopropyl)-3-ethylcarbodiimide or N,N'-dicyclohexylcarbodiimide, may be employed, advantageously in the presence of a catalyst such as a N-hydroxy compound e.g. a N-hydroxytriazole such as 1-hydroxybenzotriazole.

Intermediates of formula (2) may be prepared using methods as described in the Examples hereinafter.

Alternatively an ester of formula (1) may undergo transesterification, preferably in the presence of an acid catalyst, to give another ester of formula (1).

Esters of formula (1) may also be prepared by coupling an amine of formula (3):

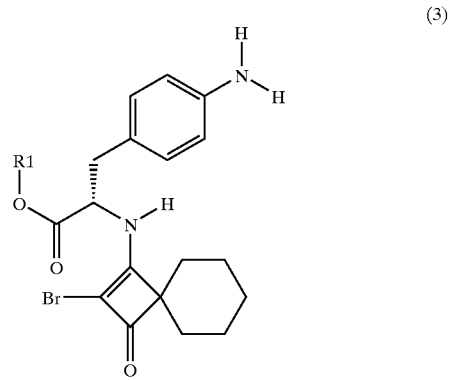

(3)

with an activated acid of formula (4):

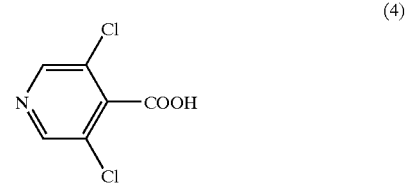

(4)

The acid of formula (4) may be activated by conversion into an acid chloride, using standard methods known to those skilled in the art, for example, as described in the Examples hereinafter. The coupling reaction may be performed in the presence of a base, such as a hydride, e.g. sodium hydride or an amine, e.g. triethylamine or N-methylmorpholine, in a solvent such as a halogenated hydrocarbon, e.g. dichloromethane or carbon tetrachloride or a dipolar aprotic solvent such as an amide, e.g. dimethylformamide or an ether, e.g. a cyclic ether such as tetrahydrofuran, at for example ambient temperature. Alternatively, the acid of formula (4) may be coupled directly with the amine of formula (3) by the use of a condensing agent, for example a diimide such as 1-(3-dimethylaminopropyl)-3-ethylcarbodiimide or N,N'-dicyclohexyl carbodiimide, advantageously in the presence of a catalyst such as a N-hydroxy compound e.g. a N-hydroxytriazole such as 1-hydroxybenzotriazole. Alternatively the acid may be reacted with a chloroformate, for example ethylchloroformate, prior to the desired acylation reaction.

Amines of formula (3) may be prepared using the general route as set out in Scheme A below.

Scheme A

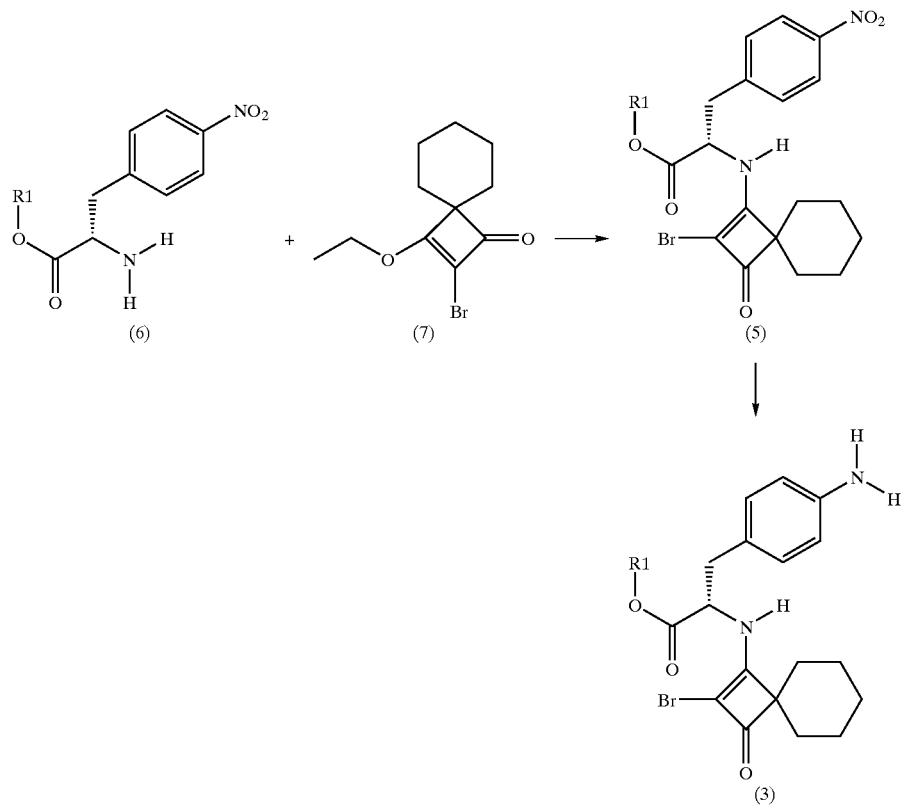

Thus, amines of formula (3) may be prepared by reduction of a nitro compound of formula (5). Suitable conditions may involve catalytic hydrogenation using for example hydrogen in the presence of a metal catalyst, for example palladium on a support such as carbon in a solvent such as an ether, e.g. tetrahydrofuran or an alcohol e.g. methanol or ethanol. The reaction may be performed at atmospheric pressure or up to a pressure of 100 ps.i. Alternatively chemical reduction using for example a metal, e.g. tin or iron, in the presence of an acid such as hydrochloric acid may be employed.

Vitro compounds of formula (5) may be prepared by reaction of a cyclobutadiene of formula (7) with an amine of formula (6). The reaction may be performed in an inert solvent or mixture of solvents, for example a hydrocarbon such as an aromatic hydrocarbon e.g. benzene or toluene and/or a halogenated hydrocarbon such as 1,2-dichloroethane, or dichloromethane at a temperature from 0° C. to the reflux temperature.

Where necessary, for example when a salt of an amine of formula (6) is used, an organic base such as diisopropylethylamine can be added.

Amines of formula (6) may be prepared using standard methods known to those skilled in the art, such as esterification of commercially available 4-nitrophenylalanine.

Intermediates of formula (7) may be prepared using methods as described in International Patent Application WO 02/068393.

In addition, N-oxides of compounds of formula (1) may be prepared for example by oxidation of the corresponding nitrogen base using an oxidising agent such as hydrogen peroxide in the presence of an acid such as acetic acid, at an elevated temperature, for example around 70° C. to 80° C., or alternatively by reaction with a peracid such as peracetic acid in a solvent, e.g. dichloromethane, at ambient temperature.

Salts of compounds of formula (1) may be prepared by reaction of a compound of formula (1) with an appropriate acid in a suitable solvent or mixture of solvents e.g. an organic solvent such as an ether e.g. diethylether, or an alcohol, e.g. ethanol using conventional procedures.

Where it is desired to obtain a particular enantiomer of a compound of formula (1) this may be produced from a corresponding mixture of enantiomers using any suitable conventional procedure for resolving enantiomers.

Thus for example diastereomeric derivatives, e.g. salts, may be produced by reaction of a mixture of enantiomers of formula (1) e.g. a racemate, and an appropriate chiral compound, e.g. a chiral base. The diastereomers may then be separated by any convenient means, for example by crystallisation and the desired enantiomer recovered, e.g. by treatment with an acid in the instance where the diastereomer is a salt.

In another resolution process a racemate of formula (1) may be separated using chiral High Performance Liquid Chromatography. Alternatively, if desired a particular enantiomer may be obtained by using an appropriate chiral intermediate in one of the processes described above. Alternatively, a particular enantiomer may be obtained by performing an enantiomer specific enzymatic biotransformation e.g. an ester hydrolysis using an esterase and then purifying only the enantiomerically pure hydrolysed acid from the unreacted ester antipode.

Chromatography, recrystallisation and other conventional separation procedures may also be used with intermediates or final products where it is desired to obtain a particular geometric isomer of the invention.

The following Examples illustrate the preparation of compounds of the invention. All temperatures are in °C. The following abbreviations are used:
NMM—N-methylmorpholine; EtOAc—ethyl acetate; MeOH—methanol; BOC—butoxycarbonyl;
DCM—dichloromethane; AcOH—acetic acid;
DIPEA—diusopropylethylamine; ETOH—ethanol;
Pyr—pyridine; Ar—aryl;
DMSO—dimethylsulphoxide; iPr—isopropyl;
$Et_2O$—diethylether; Me—methyl;
THF—tetrahydrofuran, DMF—N,N-dimethylformamide;
HOBT—1-hydroxybenzotriazole; FMOC—9-fluorenylmethoxycarbonyl;
DBU—1,8-Diazabicyclo[5,4-0]undec-7-ene;
DMAP—4-(dimethylamino)pyridine.

All NMR's were obtained either at 300 MHz or 400 MHz. All Intermediates and Examples were named with the aid of Beilstein Autonom (available from MDL Information Systems GmbH, Therdor-Heuss-Allee 108D 60486, Frankfurt, Germany) or were given names that seemed consistent, with the exception that propanoates were named by the IUPAC name rather than the trivial name (propionate) and isonicotinoyl (trivial name) is used in place of pyridine-4-carbonyl.

Intermediate 1 3,5-Dichloropyridine-4-carboxylic Acid

A solution of 3,5-dichloropyridine (5.00 g, 33.8 mmol) in THF (25 ml) was added to a solution of LDA [generated from nBuLi (2.5M solution in hexanes, 14.9 ml, 37.2 mmol) and diisopropylamine (4.10 g, 5.7 ml, 40.6 mmol)] in THF (25 ml) at −78° under nitrogen, to give a yellow/brown slurry. The reaction was stirred for 30 min at −78° then $CO_2$ gas was bubbled through to give a clear brown solution that slowly gave a precipitate, warmed to room temperature over 2 h, then quenched with water (20 ml) and partitioned between $Et_2O$ (100 ml) and 1M NaOH (100 ml). The aqueous layer was separated and acidified to pH 1 with concentrated hydrochloric acid and then extracted with 10% MeOH in DCM (100 ml×3). The combined organic layers were dried ($MgSO_4$) and the solvent removed under vacuum to give a brown solid that was recrystallised from ethanol and dried under vacuum to give the title compound as pinkish crystals (2.63 g, 41%). 8H (DMSO-d$^6$) 8.74 (2H, s). δC (DMSO-d$^6$) 163.5, 147.7, 141.0, 126.7.

Intermediate 2 Ethyl (2S)-2-[(tert-butoxycarbonyl)amino]-3-{4-[(3,5-dichloroisonicotinoyl)amino]phenyl}propanoate A slurry of the compound of Intermediate 1 (51.2 g, 0.267 mol) in DCM (195 ml) and thionyl chloride (195 ml, 2.67 mol) was treated with DMF (5 drops) and heated to reflux for 4 h. The reaction was concentrated in vacuo and azeotroped with toluene (2×50 ml) to give a yellow solid which was used without further purification. A solution of ethyl-(S)-3-(4-aminophenyl)-2-(t-butoxycarbonylamino) propanoate (130.8 g, 0.425 mol) in DCM (800 ml) was cooled to 0° and treated with NMM (56.0 ml, 0.51 mol), stirred for 5 minutes and then a solution of the acid chloride (98.3 g, 0.468 mol) in DCM (200 ml) was added dropwise keeping the reaction temperature below 5°. The reaction was stirred for 1 h, quenched with $NaHCO_3$ solution (500 ml), the organic layer separated, washed with $NaHCO_3$ solution (500 ml), 10% citric acid solution (500 ml) and $NaHCO_3$ solution (500 ml), dried ($MgSO_4$) and concentrated in vacuo to give a yellow solid which was recrystallised (EtOAc/hexane) to give the title compound, (140 g, 69%). δH (DMSO d$^6$), 8.8 (2H, s), 7.55 (2H, d, J 8.5 Hz), 7.23 (2H, d, J 8.5 Hz), 4.0 (3H, m), 3.4 (2H, b s), 2.9 (1H, m), 2.8 (1H, m), 1.3 (9H, s), 1.25 (3H, t); m/z (ES$^+$, 70V) 504 (MNa$^+$).

Intermediate 3 Ethyl (2S)-2-amino-3-{4-[(3,5-dichloroisonicotinoyl)amino]phenyl}propanoate Hydrochloride A solution of the compound of Intermediate 2 (70 g, 0.146 mol) in EtOAc (500 ml) and 1,4-dioxan (50 ml) was treated with a solution of HCl in EtOAc (500 ml, 3M), and stirred at room temperature for 4 h. The reaction was concentrated in vacuo to give a yellow solid which was triturated with $Et_2O$ then recrystallised (EtOAc/hexane) to give the title compound (59.3 g, 92%). δH (DMSO d$^6$), 11.10 (1H, s), 8.70 (2H, s), 7.55 (2H, d, J 8.4 Hz), 7.25 (2H, d, J 8.4 Hz), 4.10 (3H, m), 3.10 (2H, m), 1.10 (3H, m); m/z (ES$^+$, 70V) 382 (MH$^+$).

Intermediate 4 Ethyl (2S)-2-(3-oxospiro[3,5]non-1-en-1-ylamino)-3-{4-[(3,5-dichloroisonicotinoyl)amino]phenyl}propanoate A solution of 1-keto-3-hydroxyspiro[3,5]-non-2-ene (400 mg, 2.6 mmol) [prepared according to the method of Wasserman, H. H. et al, J. Org. Chem., 38, 1451–1455 (1973)] and the free amine of intermediate 3 (400 mg, 1.04 mmol) in THF (10 ml) was stirred at room temperature for 48 h. The volatiles were removed in vacuo and the residue chromatographed ($SiO_2$; EtOAc) to give the title compound as a white powder (512 mg, 0.99 mmol, 95%). δH (CDCl$_3$, 300K) 10.86 (1H, s), 8.78 (2H, s), 8.34 (1H, d, J 8.5 Hz), 7.56 (2H, d, J 8.5 Hz), 7.25 (2H, d, J 8.5 Hz), 4.36 (1H, s), 4.20–4.11 (3H, m), 3.13 (1H, dd, J, 13.8, 5.3 Hz), 3.00 (1H, dd, J, 9.2, 13.8 Hz), 1.67–1.19 (10H, m), 1.17 (3H, t, J, 4.1 Hz); m/z (ES$^+$, 70V) 516.0 and 518.0 (MH$^+$).

Intermediate 5 Ethyl(2S)-2-(2-bromo-3-oxospiro[3,5]non-1en-1-ylamino)-3-{4-[(3,5dichloroisonicotinoyl)amino]phenyl}propanoate A solution containing Intermediate 4 (500 mg, 0.97 mmol) and triethylamine (2 eq, 270 μl) in THF (10 ml) at 0° was treated dropwise with a solution of bromine (1.1 eq, 170 mg) in THF (5 ml). After 20 mins the reaction was allowed to warm to room temperature prior to dilution with EtOAc (100 ml). The crude reaction mixture was washed with saturated aqueous $NaHCO_3$ (20 ml) and brine (20 ml), dried ($MgSO_4$) filtered and concentrated in vacuo. The residual foam was chromatographed ($SiO_2$; EtOAc) to give the title compound as a white powder (511 mg, 0.86 mmol, 95%). δH (CDCl$_3$, 300K) 8.48 (2H, s), 8.05 (1H, s br), 7.52 (2H, d J 8.4 Hz), 7.04 (2H, d J 8.5 Hz), 5.81 (1H, d br, J 8.3 Hz), 4.98–4.91 (1H, m), 4.21 (2H, q, J 7.1 Hz), 3.21 (2H, d J 5.3 Hz), 1.70–1.66 (4H, m), 1.53–1.44 (4H, m), 1.28 (3H, t J 7.1 Hz), 1.20–1.16 (2H, m); m/z (ES$_+$, 70V) 597.9 and 595.0 (MH$^+$).

Intermediate 6 (2S)-2-(2-Bromo-3-oxospiro[3,5]non-1-en-1-ylamino)-3-{4-[(3,5-dichloroisonicotinoyl)amino]phenyl}propanoic Acid The compound of intermediate 5 (511 mg, 0.86 mmol) in THF (5 ml) was treated in a single portion with LiOH.H$_2$O (50 mg, 1.19 mmol) in H$_2$O (1 ml) and the reaction stirred at room temperature for 2 h. The reaction was then quenched by the addition of HOAc (glacial, 1 ml) and the volatiles removed in vacuo. Water (10 ml) was then added to the residue to effect precipitation. The precipitate was collected by vacuum filtration and the residue washed with water (2×5 ml). Drying under vacuum gave the title compound as a fine white solid (421 mg, 0.74 mmol, 87%). δH (DMSO d$^6$, 390K) 10.34 (1H, s), 8.67 (2H, s), 7.53 (2H, s br), 7.26 (2H, d J 8.26 Hz), 4.67 (1H, m), 3.26–3.22 (1H, m), 3.13–3.08 (1H, m), 1.67–1.21 (10H, m); m/z (ES$^+$, 70V) 569.9 and 567.9 (MH$^+$).

EXAMPLE 1

2-Hydroxyethyl (2S)-2-(2-bromo-3-oxo-spiro[3,5] non-1-en-1-ylamino)-3-{4-[(3,5-dichlorolsonicotinoyl)amino]phenyl}propanoate To a solution of the compound of Intermediate 6 (0.5 g, 0.89 mmol) in DMF (2 ml) was added EDC (190 mg, 0.97 mmol), HOBT (140 mg, 1.03 mmol) and ethylene glycol (2.5 ml). The mixture was stirred at room temperature for 48 h then partitioned between EtOAc (15 ml) and water (10 ml). The aqueous layer was separated and the organics washed with water (3×5 ml), brine (10 ml), dried ($Na_2SO_4$), filtered and concentrated in vacuo to give a crude solid. The crude was chromatographed ($SiO_2$, EtOAc) to give the title compound as a white powder (287 mg, 53%). δH (300 MHz, DMSO $d^6$) 8.88 (t H, d, J 9.2 Hz), 8.79 (2H, s), 7.59 (1H, d, J 8.5 Hz), 7.26 (2H, d, J 8.5 Hz), 4.86 (1H, m), 3.62 (1H, m), 3.25 (1H, dd, J 14.0, 4.6 Hz), 3.04 (1H, dd, J 14.0, 9.4 Hz), 1.58–1.79 (6H, m), 1.37 (1H, d, J=12.7 Hz), 1.11 (2H, br); m/z ($ES^+$, 70V) 610 ($MH^+$).

EXAMPLE 2

Methyl (2S)-2-(2-bromo-3-oxo-spiro[3,5]non-1-en-1-ylamino)-3-{4-[(3,5-dlchloroisonicotinoyl)amino]phenyl}propanoate Using a similar procedure to that for the preparation of the ester of Example 1 [acid (0.50 g, 0.9 mmol), EDC (0.19 g), HOBT (0.14 g), methanol (1.0 ml), DMF (5 ml)] was prepared the title compound (0.42 g, 80%). $^1$H NMR (400 MHz, d6 DMSO) δ 1.17 (2H, br), 1.38 (1H, d, J=11.8 Hz), 1.58–1.80 (7H, m), 3.05 (1H, dd, J=9.6, 14.8 Hz), 3.25 (1H, dd, J=4.6, 14.0 Hz), 3.78 (3H, s), 3.62 (1H, m), 4.87 (1H, m), 7.29 (2H, d, J=8.4 Hz), 7.62 (2H, d, J=8.4 Hz), 8.83 (2H, s), 8.95 (1H, d, J=9.2 Hz). m/z (ESI, 70V) MH+580.

EXAMPLE 3

Butyl (2S)-2-(2-bromo-3-oxo-spiro[3,5]non-1-en-1-ylamino)-3-{4-[(3,5-dichloroisonicotinoyl)amino]phenyl}propanoat Using a similar procedure to that for the preparation of the ester of Example 1 [acid (0.50 g, 0.9 mmol), EDC (0.19 g), HOBT (0.14 g), n-butanol (1.0 ml), DMF (5 ml)] was prepared the title compound (0.48 g, 86%). $^1$H NMR (400 MHz, d6 DMSO) δ 0.91 (3H, t, J=7.4 Hz), 1.18 (1H, br), 1.47–1.82 (13H, m), 3.09 (1H, dd, J=9.6, 13.8 Hz), 3.25 (1H, dd, J=5.1, 13.8 Hz), 4.18 (2H, t, J=6.3), 4.84 (1H, m), 7.31 (2H, d, J=8.5 Hz), 7.62 (2H, d, J=8.5 Hz), 8.84 (2H, s), 8.95 (1H, d, J=9.1 Hz). m/z (ESI, 70V) MH+622.

The following cellular assays can be used to demonstrate the potency and selectivity of the compounds according to the invention. In each of these assays an $IC_{50}$ value was determined for each test compound and represents the concentration of compound necessary to achieve 50% inhibition of cell adhesion where 100%=adhesion assessed in the absence of the test compound and 0%=absorbance in wells that did not receive cells.

$\alpha_4\beta_1$ Integrin-Dependent Jurkat Cell Adhesion to VCAM-Ig 96 well NUNC plates were coated with F(ab)$_2$ fragment goat anti-human IgG Fcγ-specific antibody [Jackson Immuno Research 109-006-098: 100 μl at 2 μg/ml in 0.1M NaHCO$_3$, pH 8.4], overnight at 4°. The plates were washed (3×) in phosphate-buffered saline (PBS) and then blocked for 1 h in PBS/1% BSA at room temperature on a rocking platform. After washing (3× in PBS) 35 ng/ml of purified 2d VCAM-1-hFc diluted in PBS/1% BSA was added and the plates left for 60 minutes at room temperature on a rocking platform. The plates were washed (3× in PBS) and the assay then performed at 37° for 30 min in a total volume of 200 μl containing 2.5×10$^5$ Jurkat cells in the presence or absence of titrated test compounds.

Each plate was washed (2×) with medium and the adherent cells were fixed with 100 μl methanol for 10 minutes followed by another wash. 100 μl 0.25% (w/v) Rose Bengal (Sigma R4507) in PBS was added for 5 minutes at room temperature and the plates washed (3×) in PBS. 100 μl 50% (v/v) ethanol in PBS was added and the plates left for 60 min after which the absorbance (570 nm) was measured.

$\alpha_4\beta_7$ Integrin-Dependent JY Cell Adhesion to MAdCAM-Ig

This assay was performed in the same manner as the $\alpha_4\beta_1$ assay except that MAdCAM-hFc (300 ng/ml) was used in place of 2d VCAM-1-hFc and a sub-line of the β-lymphoblastoid cell-line JY was used in place of Jurkat cells. The $IC_{50}$ value for each test compound was determined as described in the $\alpha_4\beta_1$ integrin assay.

$\alpha_5\beta_1$ Integrin-Dependent K562 Cell Adhesion to Fibronectin 96 well tissue culture plates were coated with human plasma fibronectin (Sigma F0895) at 5 μg/ml in phosphate-buffered saline (PBS) for 2 hr at 37° C. The plates were washed (3× in PBS) and then blocked for 1 h in 100 μl PBS/1% BSA at room temperature on a rocking platform. The blocked plates were washed (3× in PBS) and the assay then performed at 37° C. in a total volume of 200 μl containing 2.5×10$^5$ K562 cells, phorbol-12-myristate-13-acetate at 10 ng/ml, and in the presence or absence of titrated test compounds. Incubation time was 30 minutes. Each plate was fixed and stained as described in the $\alpha_4\beta_1$ assay above.

$\alpha_m\beta_2$-Dependent Human Polymorphonuclear Neutrophils Adhesion to Plastic 96 well tissue culture plates were coated with RPMI 1640/10% FCS for 2 h at 37° C. 2×10$^5$ freshly isolated human venous polymorphonuclear neutrophils (PMN) were added to the wells in a total volume of 200 μl in the presence of 10 ng/ml phorbol-12-myristate-13-acetate, and in the presence or absence of test compounds, and incubated for 20 min at 37° C. followed by 30 min at room temperature. The plates were washed in medium and 100 μl 0.1% (w/v) HMB (hexadecyl trimethyl ammonium bromide, Sigma H5882) in 0.05M potassium phosphate buffer, pH 6.0 added to each well. The plates were then left on a rocker at room temperature for 60 min. Endogenous peroxidase activity was then assessed using tetramethyl benzidine (TMB) as follows: PMN lysate samples mixed with 0.22% $H_2O_2$ (Sigma) and 50 μg/ml TMB (Boehringer Mannheim) in 0.1M sodium acetate/citrate buffer, pH 6.0 and absorbance measured at 630 nm.

$\alpha IIb/\beta_3$-Dependent Human Platelet Aggregation

Human platelet aggregation was assessed using impedance aggregation on the Chronolog Whole Blood Lumiaggregometer. Human platelet-rich plasma (PRP) was obtained by spinning fresh human venous blood anticoagulated with 0.38% (v/v) tri-sodium citrate at 220×g for 10 min and diluted to a cell density of 6×10$^8$/ml in autologous plasma. Cuvettes contained equal volumes of PRP and filtered Tyrode's buffer (g/liter: NaCl 8.0; MgCl$_2$.H$_2$O 0.427; CaCl$_2$ 0.2; KCl 0.2; D-glucose 1.0; NaHCO$_3$ 1.0; NaHPO$_4$.2H$_2$O 0.065). Aggregation was monitored following addition of 2.5 μM ADP (Sigma) in the presence or absence of inhibitors.

In the above assays compounds of the invention such as the compounds of the Examples generally have $IC_{50}$ values in the $\alpha_4\beta_1$ assay of 1 μM and below and in the $\alpha_4\beta_7$ assay of 5 μM and below. Thus for example the compound of Example 1 has an $IC_{50}$ value of 4 nM in the $\alpha_4\beta_1$ assay.

What is claimed is:

1. A compound of formula (1):

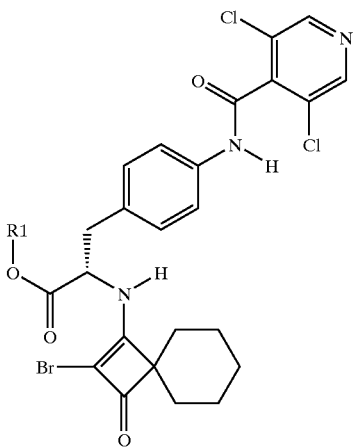
(1)

wherein $R^1$ is a —CH$_3$, —(CH$_2$)$_3$CH$_3$, —CH$_2$CH$_2$OH, —CH$_2$CH$_2$OCH$_3$, —CH$_2$CH$_2$OCH$_2$CH$_2$OH, —CH$_2$CH$_2$OCH$_2$CH$_2$OCH$_3$,

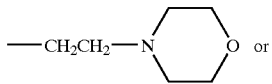 or

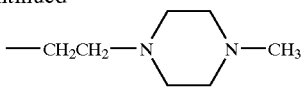

group;

and the salts, solvates and N-oxides thereof.

2. A compound according to claim 1 which is butyl (2S)-2-(2-bromo-3-oxo-spiro[3,5]non-1-en-1-ylamino)-3-{4-[(3,5-dichloroisonicotinoyl)amino]phenyl}propanoate and the salts, solvates and N-oxide thereof.

3. A compound which is butyl (2S)-2-(2-bromo-3-oxo-spiro[3,5]non-1-en-1-ylamino)-3-{4-[(3,5-dichloroisonicotinoyl)amino]phenyl}propanoate.

4. A compound according to claim 1 which is 2-hydroxyethyl (2S)-2-(2-bromo-3-oxo-spiro[3,5]non-1-en-1-ylamino)-3-{4-[(3,5-dichloro isonicotinoyl)amino]phenyl}propanoate and the salts, solvates and N-oxide thereof.

5. A compound which is 2-hydroxyethyl (2S)-2-(2-bromo-3-oxo-spiro[3,5]non-1-en-1-ylamino)-3-{4-[(3,5-dichloroisonicotinoyl) amino]phenyl}propanoate.

6. A compound according to claim 1 which is methyl (2S)-2-(2-bromo-3-oxo-spiro[3,5]non-1-en-1-ylamino)-3-{4-[(3,5-dichloroisonicotinoyl) amino]phenyl}propanoate and the salts, solvates and N-oxide thereof.

7. A compounds which is methyl (2S)-2-(2-bromo-3-oxo-spiro[3,5]non-1-en-1-ylamino)-3-{4-[(3,5-dichloroisonicotinoyl) amino]phenyl}propanoate.

8. A pharmaceutical composition comprising a compound according to any of claims 1 to 7 together with one or more pharmaceutically acceptable carriers, excipients or diluents.

* * * * *

UNITED STATES PATENT AND TRADEMARK OFFICE
CERTIFICATE OF CORRECTION

PATENT NO. : 6,872,719 B1
APPLICATION NO. : 10/620533
DATED : March 29, 2005
INVENTOR(S) : Julien Alistair Brown, Stuart Bailey and Stephen Brand It is certified that error appears in the above-identified patent and that said Letters Patent is hereby corrected as shown below:

On the Title page, under "Other Publications" please delete "Tiskin" and insert --Briskin--

On Page 2, in the second column, under the Wasserman reference, please delete "ethoxyacety;ene" and insert --ethoxyacetylene--

In Column 1, Line 64, please delete "et a," and insert --et al,--

In Column 2, Line 24, please delete "et at," and insert --et al,--

In Column 2, Line 47, please delete "Birskin" and insert --Briskin--

In Column 3, Lines 60 and 64, please delete "3,5" and insert --3.5--

In Column 4, Lines 1, 5, 10, 14 and 22, please delete "3,5" and insert --3.5--

In Column 7, Line 46, please delete "Vitro" and insert --Nitro--

In Column 9, Line 9, please delete "diusopropylethylamine" and insert --diiusopropylethylamine--

In Column 9, Line 9, please delete "ETOH" and insert --EtOH--

In Column 9, Line 44, please delete "8H" and insert --δH--

In Column 10, Lines 14, 31 and 50, please delete "3,5" and insert --3.5--

In Column 10, Line 52, please delete "Acid" and insert --acid--

In Column 11, Lines 3, 24 and 40, please delete "3,5" and insert --3.5--

In Column 11, Line 17, please delete "(t H," and insert --(1 H,--

UNITED STATES PATENT AND TRADEMARK OFFICE
CERTIFICATE OF CORRECTION

PATENT NO. : 6,872,719 B1
APPLICATION NO. : 10/620533
DATED : March 29, 2005
INVENTOR(S) : Julien Alistair Brown, Stuart Bailey and Stephen Brand It is certified that error appears in the above-identified patent and that said Letters Patent is hereby corrected as shown below:

In Column 11, Line 26, please delete "dlchloroisonicotinoyl" and insert "dichloroisonicotinoyl"

In Column 11, Line 43, please delete "propanoat" and insert --propanoate--

In Column 14, Lines 10, 14, 17, 22, 25 and 29, please "[3,5]" and insert --[3.5]--

In Column 14, Line 28, please delete "compounds" and insert --compound--.

Signed and Sealed this

Fifteenth Day of August, 2006

JON W. DUDAS
*Director of the United States Patent and Trademark Office*